United States Patent
Hartley et al.

(10) Patent No.: US 6,921,906 B2
(45) Date of Patent: Jul. 26, 2005

(54) MASS SPECTROMETER

(75) Inventors: Frank T. Hartley, Arcadia, CA (US); Steven J. Smith, Canyon County, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 10/400,130

(22) Filed: Mar. 25, 2003

(65) Prior Publication Data

US 2003/0201387 A1 Oct. 30, 2003

Related U.S. Application Data

(63) Continuation-in-part of application No. 10/184,089, filed on Jun. 25, 2002.
(60) Provisional application No. 60/301,092, filed on Jun. 25, 2001.

(51) Int. Cl.[7] .................................................. H01J 27/02
(52) U.S. Cl. .............................. 250/423 F; 250/423 R; 313/230
(58) Field of Search ........................ 250/423 F, 423 R; 313/230

(56) References Cited

U.S. PATENT DOCUMENTS 4,926,056 A * 5/1990 Spindt .................... 250/423 F

* cited by examiner

Primary Examiner—Nikita Wells
Assistant Examiner—Paul M. Gurzo
(74) Attorney, Agent, or Firm—Christie, Parker & Hale, LLP

(57) ABSTRACT

A rotating field mass spectrometer includes an ionizing structure having a pair of conductive electrodes located closer to one another than the mean free path of the gas being ionized, and a rotating field mass spectrometer part for analyzing ions produced by the ionizing structure. The membrane may include a supporting portion, and a relatively thin non-supporting portion where the ions are formed.

23 Claims, 4 Drawing Sheets

MASS SPECTROMETER

CROSS-REFERENCE TO RELATED APPLICATIONS

This application is a continuation-in-part of U.S. patent application Ser. No. 10/184,089, filed Jun. 25, 2002, which claims the benefit of U.S. Provisional Application 60/301,092, filed on Jun. 25, 2001.

STATEMENT REGARDING FEDERALLY SPONSORED RESEARCH OR DEVELOPMENT

The invention described herein was made in the performance of work under a NASA7-1407 contract, and is subject to the provisions of Public Law 96-517 (U.S.C. 202) in which the contractor has elected to retain title.

BACKGROUND

Generally, in mass spectrometer systems, atoms and molecules present in a subject sample are ionized, i.e., converted into ions, and introduced into a mass spectrometer where the ionic species are separated according to their mass-to-charge ratio. A charged-particle detector located at the exit of the mass spectrometer counts the separated ions in order to identify the mass and velocity distribution of ions in an ion beam. From this, information useful in determining the chemical composition of the sample can be determined.

Mass spectrometers are known in the prior art. However, these prior art systems exhibit several drawbacks. For example, many employ magnetic fields and therefore inherently require bulky magnets and shielding while others require precise machining and placements of the various mass spectrometer components such as multi-pole rods. Because of these requirements, prior art devices may not be easily miniaturized and therefore are not amenable to the next generation of millimeter and sub-millimeter-sized spectrometers. Such miniaturized and micro-machined instruments are desired and needed. Examples of use include pollution monitoring in factories, homes, auto exhausts, residual gas analysis and plasma processing, as well as and on spacecraft, for low-mass, low-power investigations of planetary environments.

As alluded to above, an important aspect of any spectrometer device or system is the ionization of the subject sample. In the spectrometric method described above, the ionization of the sample plays an important role and may dictate limitations on the use of the mass spectrometer device. Generally, there are two types of ionization techniques, typically referred to as "soft" ionization and "hard" ionization. The label of "soft" or "hard" refers to the degree of fragmentation of molecular ions in the ionization process. In "soft" methods, there is a minimum or negligible amount of ion fragmentation as opposed to "hard" methods where the degree of molecular ion fragmentation is much higher. Soft ionization methods often provide advantages over hard methods and are therefore desirable for many applications. For example, using soft ionization techniques, inorganic and organic compounds may be analyzed with the preservation of supramolecular assemblies.

Conventional prior art mass spectrometers often use "hard" techniques of producing ions, in which molecules are forcibly fractured. For example, ions may be produced by ultraviolet, radioactive, and/or thermal electron bombardment ionization techniques. As discussed above, these "hard" methods result in a significant degree of molecular ion fragmentation and may be undesirable in applications where the preservation of the molecular ion integrity is beneficial or even necessary.

Different mass spectrometer systems using ionization are known in the art. For example, quadrapole, magnetic sector and time of flight systems ionize sample material to determine its compositional content. Each of these devices have certain limitations in both operational use and size, however. For example, the quadrapole and magnetic section devices have relatively low resolution and therefore are limited in their compositional analyzing capabilities. These devices may also suffer from the standpoint of efficiency, especially during the ionization process.

Another disadvantage of prior art mass spectrometers utilizing hard ionization methods is that such systems generally require a high vacuum ($10^{-5}$ Torr or better) environment. One reason for such a requirement is to enhance the life of the filament source. Secondly, and more importantly, a high vacuum environment is required so that ion collisions can be avoided during passage through the mass spectrometer device. With such rigorous demands, a vacuum pump must be provided to maintain a high vacuum under a variety of sample load conditions.

Vacuum pumps also consume power, may be heavy, large and typically require a relatively leak free environment. These limitations and necessities resulting from the need for a vacuum environment, and therefore the need for a vacuum pump, hinder the desired goal of instrument miniaturization.

Other desirable applications may be achieved and may benefit from the use of ionization systems if such systems were sufficiently small. However, existing ionization systems exhibit problems and difficulties in fabrication on smaller scales and therefore have not been suitable for use in these other desirable applications.

One particular form of mass spectrometer is disclosed in U.S. Pat. No. 5,726,448 to Smith et al. This device, called a rotating field mass spectrometer, provides a mass and velocity analyzer that utilizes time dependent electric fields to guide the ions being detected. Thus, precision ion beam apparatuses are not required.

SUMMARY OF THE INVENTION

The present invention is directed to a spectrometer apparatus for analyzing compounds and more particularly to a novel mass spectrometer having a structure providing soft ionization of a subject sample. In one embodiment, the ionizing structure is a membrane structure having a plurality of apertures, with a sub-micron gap separating a pair of electrodes at each of the plurality of apertures. According to one aspect of the invention, the electrodes of the ionizing structure are separated by a distance smaller than the mean free path of the gas molecules under particular pressure and temperature conditions. With such an electrode gap, the sample gas may be ionized without fragmentation, i.e., soft ionization may be accomplished.

An embodiment of the invention incorporates the ionizing structure into a rotating field mass spectrometer. In this combination, the rotating field mass spectrometer is rendered useful in applications that require soft ionization of a subject sample, thereby broadening the utility of such a device. In addition, this combination takes advantage of the fact that rotating field mass spectrometers are amenable to miniaturization down to sub-millimeter dimensions and, unlike many other mass spectrometers, do not require a high degree of precision for manufacture.

In another embodiment, a "pumpless" mass spectrometer is described, i.e., a mass spectrometer that does not include a pump for either forming the vacuum or driving the neutral medium. In a closed system, where all incoming vapor passes through the ionizing structure and is totally ionized, there will be fewer molecules traveling at thermal velocities and attenuation will be less. Accelerating the ions away from the ionizing structure then creates a partial vacuum downstream of the membrane, eliminating the need for a vacuum pump.

BRIEF DESCRIPTION OF THE DRAWINGS

These and other aspects of the invention will now be described in detail with reference to the accompanying drawings, wherein.

DETAILED DESCRIPTION OF THE INVENTION

It is known that a gas may be ionized when subject to a high electric field. However, one drawback of this ionization method is that an undesirable phenomenon, known as avalanche breakdown, may occur. At the point of avalanche, ion fragmentation begins to occur during the ionization process. This phenomenon is well known and has been a major concern in the development of ionization devices and other apparatus utilizing the same.

It has been discovered that avalanche arcing may be minimized or even eliminated when the electrodes of an ionizing structure are separated such that the separation distance or "gap" is smaller than the "mean free path" distance between molecules of a gas to be ionized. In such a configuration, ions that are accelerated by high voltages rarely encounter neutral atoms of low pressure residual gas. Thus, the secondary ionization avalanche process of breakdown is inhibited and only ionization occurs.

Figure 1:
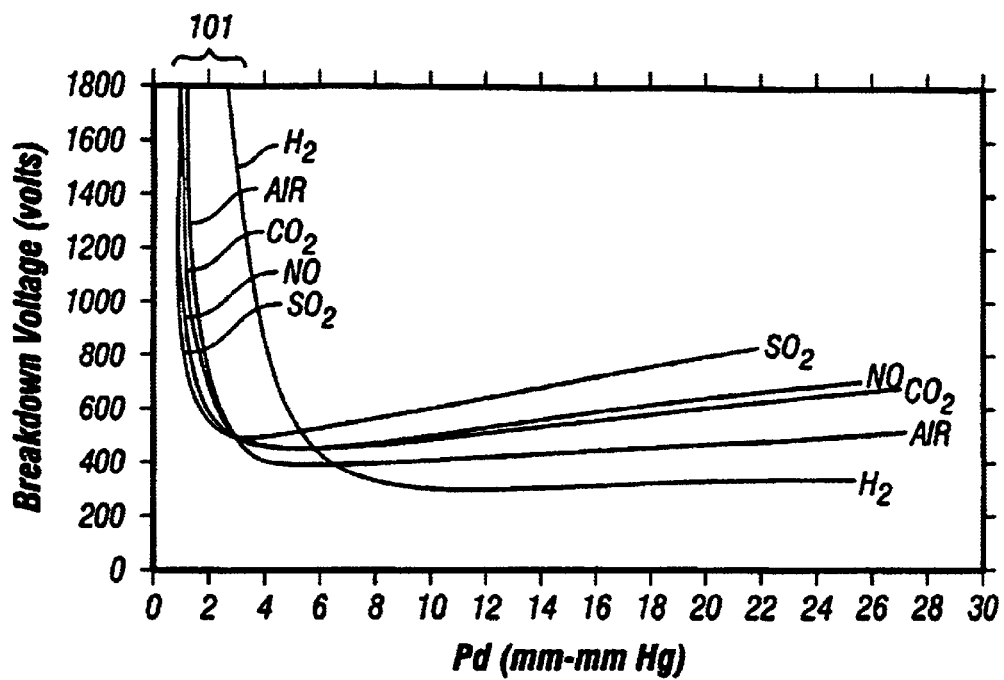
FIG. 1, in plot form, depicts the Paschen curves for various gases, as recreated from the work of F. Paschen.

Referring now to FIG. 1, a graphical plot depicts the Paschen curves for various gases, including $H_2$, $H_2O$, $CO_2$, NO and $SO_2$. This represents the breakdown voltage of each gas as a function of the product of electrode separation and gas pressure (Pd). Where the separation is maintained such that Pd is small for all pressures, i.e. beneath the Paschen curve, ionization occurs without unwanted damage to the sample, that is, fragmentation does not occur. Therefore, the separation distance between electrodes of the ionizing structure may be selected such that only ionization occurs without avalanche breakdown. As previously mentioned, this is the case where the electrode separation distance is smaller than the mean free path between the gas molecules.

As will be described further below, gas ionization may occur using the ionizing structure of the present invention. The ionization technique described herein using the ionizing structure is considered a "soft" ionization method because there is a minimum amount of ion fragmentation in the ionization process.

Figure 2A:
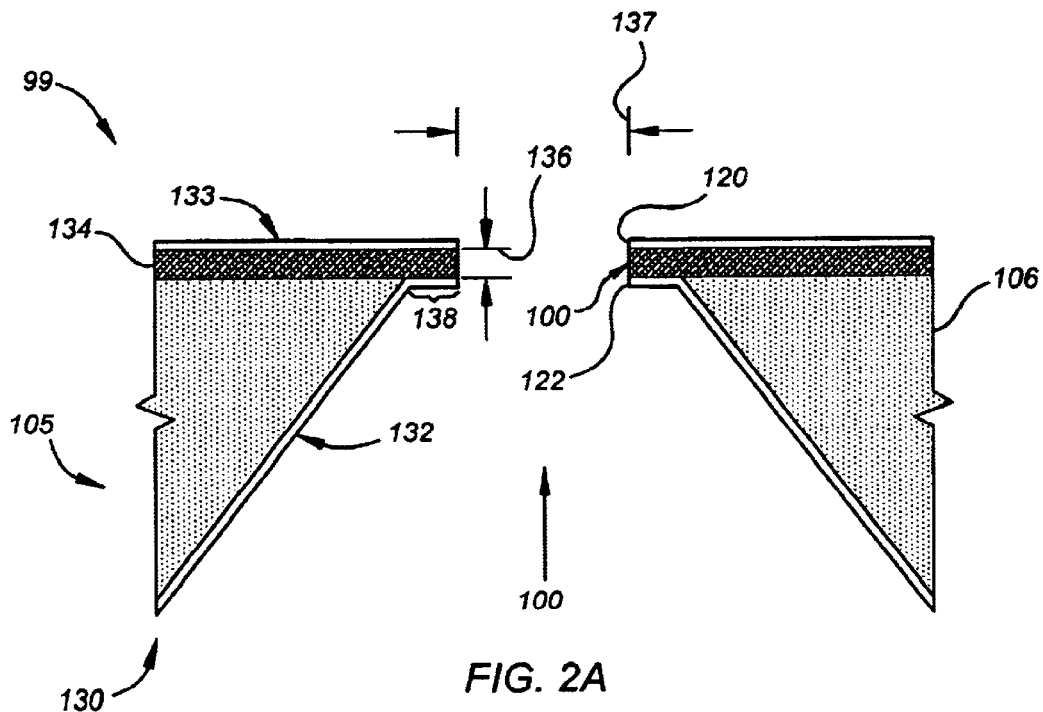
FIG. 2A is an enlarged fragmentary cross-sectional view depicting one form of the ionizing structure of FIG. 2C in the region of one of its apertures.
Figure 2B:
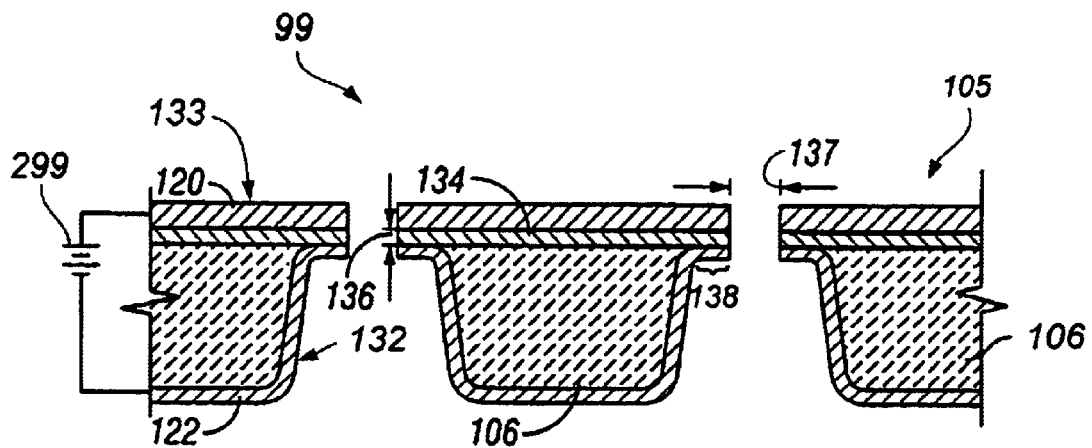
FIG. 2B is an enlarged fragmentary cross-sectional view depicting another form of the ionizing member of FIG. 2C taken along the line 2B—2B.
Figure 2C:
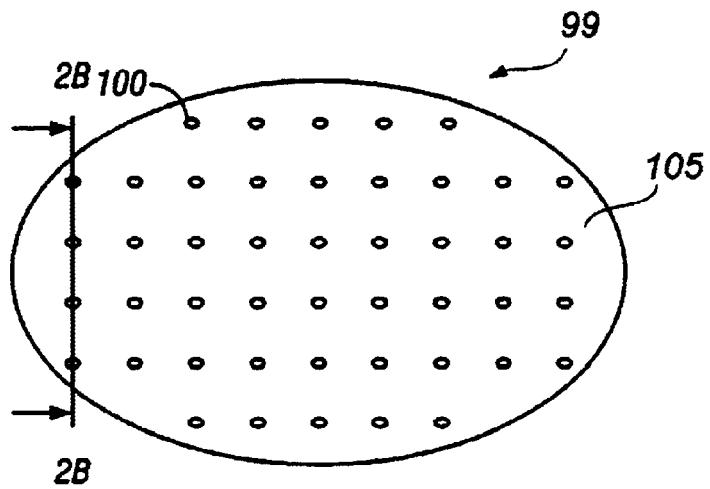
FIG. 2C, in plan view, depicts an ionizing structure constructed according to an embodiment of the present invention.

Referring now to FIGS. 2A–2C, details of an ionizing structure are shown. For ease of describing the novel features of the present invention, FIGS. 2A & 2B show the structure of FIG. 2C in cross section, and similar elements are given similar reference numerals.

Referring specifically to FIG. 2C, the ionizing structure 99 may be formed by micro-machining or otherwise forming an array of small apertures 100 through relatively thin regions of a membrane structure 105. The membrane structure 105 in the regions of the apertures may be extremely thin, for example, having sub-micron thickness.

Referring now to FIG. 2b, the membrane structure 105 may comprise a number of material layers. In this particular embodiment, a physical support structure 106 is provided in the form of a substrate of silicon or other suitable material several tens of microns thick that may be easily machined or otherwise treated to create the desired support configuration. For example, the techniques used for forming the support structure may be any of those known in the art for fabricating microelectromechanical machines (MEMS). Additional layers forming electrically conductive electrodes 120 and 122 are located on respective sides of the membrane layer 134 such that the support structure 106 is sandwiched between the electrodes 120 and 122. The electrodes 120 and 122 may be made of a metallic material, such as, for example, chrome, titanium or gold, or any suitable non-metallic conductor.

The membrane structure 99 also includes an insulating layer 134 located between the upper electrode 120 and the support structure 106. The insulating layer may be made of a suitable dielectric material such as, for example, silicon nitride, alumina, or any other comparable material that has a high dielectric breakdown. In one embodiment, the dielectric material has a dielectric breakdown of at least $10^7$ volts/meter, and in another form $10^8$–$10^9$ volts/meter. The material may be deposited by any suitable process such as, for example, chemical vapor deposition (CVD).

In the embodiment of FIG. 2B, the insulating layer 134 may be recessed in the area directly adjacent the apertures 100 such that the thickness 136 of the insulating layer sets the distance, i.e., the gap separation, between the top and bottom electrodes 120 and 122 over a region 138 surrounding each of the plurality of apertures 100. The thickness 136 of the insulating layer in one embodiment of the invention is between 200 and 300 nm. However, it is noted that the thickness 136 may be chosen outside the 200–300 nm range and may be, for example, less than 200 nm, and in some cases as thin as 50 nm. When gap separations on this order are maintained, electric field strengths on the order of mega volts per meter can be produced at the apertures for each volt of potential difference between the top and bottom electrodes 120, 122.

Referring now to FIG. 2A, the membrane structure 105 may have a top surface 133 and a bottom surface 132. In the formation of the ionizing structure 99, each of the plurality of apertures 100 may be formed from the bottom surface 132 and penetrating through the top surface 133, or vice versa, such that the apertures 100 are of substantially uniform diameter between their upper and lower ends. The diameter of the apertures 100 formed in this way may be, for example, 2 to 3 microns. The regions surrounding the apertures may then be at least a few microns in width, giving the membrane structure 105 a relatively thin portion approximately 10 microns or more in diameter surrounding each of the apertures 100. These openings may be formed in the top conductive coating 120, the bottom conductive coating 122 and the insulating. layer 134, by any suitable method known in the fields of semiconductor or thin film materials processing. For example, the apertures may be formed by focused ion-beam milling, a maskless process.

Referring back to FIG. 2B, it is noted that it would be possible, although not often desirable, to form the ionizing structure 105 entirely from thin, sub micron elements of the type found at the regions 138 surrounding the apertures 100. Membranes formed in this way may be too fragile to sustain a pressure difference across them in some cases, however, or to survive minor mechanical shocks. That is why the embodiments of FIGS. 2A and 2B have a supporting substrate 106 which is thicker than the combination of the insulating layer 134 and the electrodes 120 and 122 at locations remote from the apertures 100. By forming the membrane structure 105 with a relatively thick substrate portion, such as 106, the structural integrity of the device may be maintained while keeping a relatively small distance or gap separation 136 between the electrodes 120 and 122 in the regions 138 surrounding the plurality of apertures 100. In the illustrated embodiment, this distance between the electrodes at the edges of the apertures 100 is less than the mean free path of the molecules to be ionized, permitting "soft" ionization without avalanche breakdown.

An embodiment will now be described that utilizes a field ionizer array, for example, the ionizing structure 99 described above, with a lateral accelerator coupled operationally to a rotating field mass spectrometer. The system so combined becomes a self-sampling mass spectrometer having no moving parts, which may be used at ambient pressures less than one Torr. Furthermore, ultraviolet, radioactive ionization or thermal electron sources are not required. The rotating field mass spectrometer has a large dynamic range which, when configured with the ionizing membrane, is suitable for use in analyzing a wide range of particles from singly-charged gas ions to compound gases and large DNA fragments.

Figure 3:
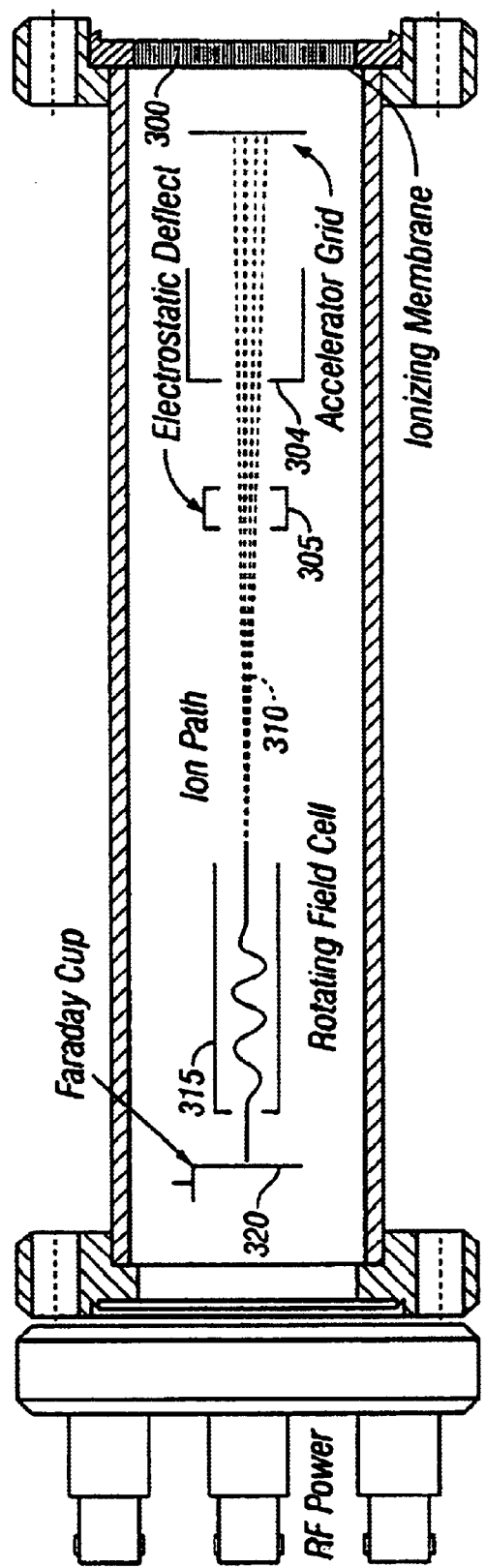
FIG. 3, in cross-sectional view, depicts a rotating field mass spectrometer utilizing the ionizing structure of FIGS. 2A–2C.

Referring now to FIG. 3, an embodiment utilizing an ionizer array in a mass spectrometer is shown. An ionizing structure 300 of the type previously described may be used. As described above, this ionizing structure includes electrodes separated by a distance less than the mean free path of the molecules to be ionized. The electrodes are supplied with a potential from a voltage source 299 (as shown in FIG. 2B.) The voltage source 299 provides a potential across the electrodes 120 and 122 resulting in an electric field on the order of megavolts per meter at a plurality of apertures through the ionizing structure, thereby causing molecules passing through the apertures to be ionized.

The ions produced by the ionizing structure 300 may then be electrostatically accelerated, deflected and focused by an accelerator grid 304 and other electrostatic elements 305, along an ion path 310.

The focused ions traveling along the ion path 310 may be launched at an angle $\Theta$ into a cavity cell 315. The cavity cell 315 may be, for example, a compact cell on the order of 2×2×20 mm. Within the cavity cell 315, the frequency $\Omega$ of the rotating electric field may be varied to scan through the desired range of ion masses. For ions injected with a launch angle $\Theta>0$ and at frequency $\Omega$, any ions that exhibit a mass/charge ratio in resonance with the currently applied electric field value follow a helical path through the mass spectrometer. For the case of $\Theta=0$, ions travel through the cell in a helical path, with the radius of the helix inversely proportional to the mass/charge ratio of the ion.

Figure 4:
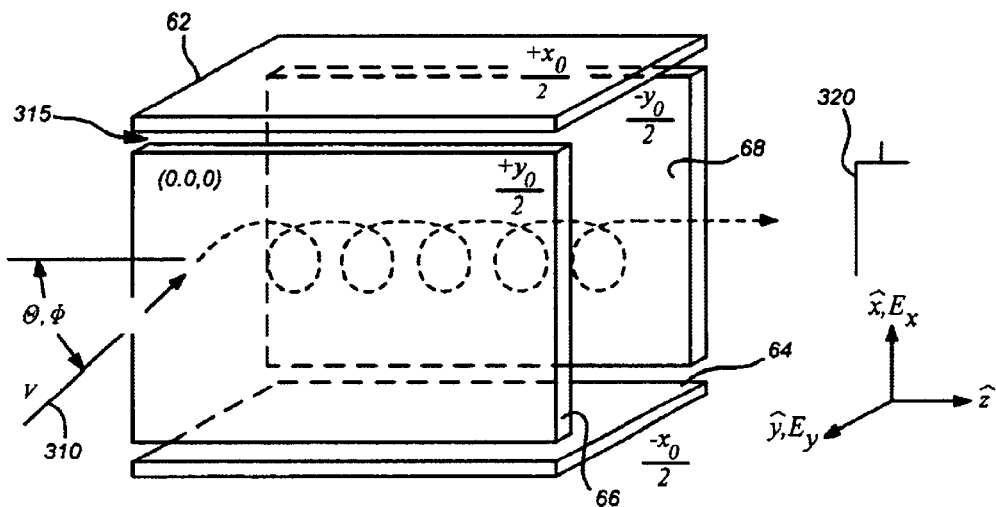
FIG. 4, in enlarged plan view, is a diagrammatic representation of ions in a helical pathway as they pass through a cavity cell of the mass spectrometer of FIG. 3.

Referring now to FIG. 4, the cavity cell 315 is shown in an enlarged view to further illustrate how the ions disperse and how the helix geometry is related to information about the ions. This cell and its operation are as described in U.S. Pat. No. 5,726,448 to S. Smith et al., the disclosure of which is hereby incorporated by reference.

The cavity cell 315 may include four walls or plates, which are shown schematically as 62, 64, 66 and 68, respectively. The four walls or plates comprise a top wall 62, a bottom wall 64, a front wall 66 and a back wall 68. The cavity cell 315 is adapted to receive an ion beam traveling along the ion path 310 previously described and shown in FIG. 3. Within the cavity cell 315, ions exhibiting a mass/charge ratio in resonance with the currently applied electric field travel in a helix formation as they pass through the cavity cell 315 and land on a Faraday cup collector 320. Ions injected at angle $\Theta$ that are not in resonance strike other elements such as the walls or plates 62, 64, 66, and 68 of the cavity cell 315 and therefore do not arrive at, nor are they collected on, the Faraday cup collector 320. Hence, the number of ions that strike the Faraday cup collector 320 indicate the number of ions exhibiting a mass/charge ratio in resonance with the currently applied electric field value. By sweeping the frequency of the electric field value across all possible frequency values, information about the ions may be determined and the content of the sample can be detected.

The frequency of resonance varies inversely with the mass of the ion. Therefore, detection of the amount or number of ions arriving at or striking the Faraday cup 320 at a particular frequency provides information about those ions.

In this system, the applied RF voltages may remain between 1 and 13 volts peak to peak, or more generally, less than 15 volts. It can be seen that the detection of different sample specimens may be accomplished by using different frequency ranges. For example, relatively lightweight gas molecules may be scanned at MHz frequencies, while larger organics, such as DNA organic material, may be scanned at kHz frequencies. In general, lighter molecules may be scanned at higher frequencies.

Figure 5:
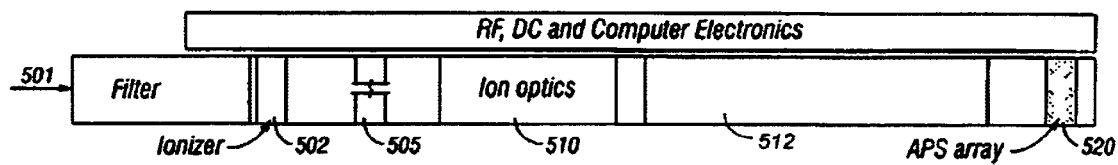
FIG. 5, in plan view, depicts a low-pressure rotating field mass spectrometer utilizing the ionizing structure of FIGS. 2A–2C and having a solid state detection device capable of creating a two-dimensional output.

An alternative mass spectrometer embodiment constructed according to the invention is shown in FIG. 5. This device uses an electronic image sensor to detect the position at which ionized particles impinge on the sensor.

In the embodiment of FIG. 5, the material 500 is input through a filter to an ionizing structure, here 502, of the type previously described. The ionized particles pass through an accelerating electrode 505, through ion optics 510, through a rotating field cell 512 which is similar to the cell 315 described above, and finally to the electrodes of a pixelated electrometer array 520. In one embodiment, the pixelated electrometer array 520 may be a modified form of an active pixel sensor array of the type described in U.S. Pat. No. 5,471,515 to E. Fossum et al., the disclosure of which is hereby incorporated by reference. The required modification of the active pixel sensor array is to remove its photonic generating dielectric and thereby bring its electrodes to the surface. In this form, the modified active pixel sensor array serves as a convenient electrode array providing two-dimensional information as to ion current. As known in the art, the pixelated electrometer array may include various types of on-chip matrix processing. Specifically, this system may use an electrode sensor of 1024 by 1024 electrodes, with sub pixel centroiding and radial integration. The electrometer array itself may have a sensitivity on the order of the charge of several electrons. By adding pixel current processing, another two orders of magnitude of sensitivity may be obtained.

Because this system provides a two-dimensional output, electrode centroiding and radial integration may be used to improve mass resolution. Thus, the system of FIG. 5 may be used for sampling particles over a wide range exending from the smallest possible ion masses (hydrogen having a mass of one atomic mass unit) to large fragments with masses greater than 10,000 AMU.

As previously noted, it has been generally believed that the use of mass spectrometers is limited to vacuum conditions of millitorr or better; however, such limitations are overcome by the present invention which provides a mass spectrometer system capable of operating at pressures of, for example, 5 to 7 Torr or higher. This ability to operate without a high vacuum results from the fact that the ionizing structure of the invention provides high ion currents that can tolerate attenuation from collisions with neutral molecules and still be measurable. Not requiring a high vacuum environment eliminates the need for a high vacuum pump. To the extent that a vacuum of any level is required, much lower power and smaller pumps operating at a few Torr can suffice. Pumps of this type include sub liter per second ion pumps and membrane mechanical pumps.

The mean free path concepts discussed herein are based on the average distance between collisions of neutral gas molecules or atoms traveling at room temperature and at a given pressure. At room temperature, the neutral gas molecules are traveling at "thermal velocities," and based on the kinetic theory that kinetic energy is equal to 3/2 kT, where T is the temperature in Kelvin, and k is the Boltzman constant, it is seen that the kinetic energy of the neutral molecules is about 1/40th of an electron volt (eV) for room temperature conditions.

By contrast, the present invention allows the production and acceleration of ions having energies up to 600 eV. The ions therefore have 2400 times the energy, and about 49 times higher velocity than the corresponding specimen neutral gas molecules. Because collision loss rates are based on "time of interaction," given that there are fewer targets, such as background residual vacuum gas molecules, to hit, lower collision loss rates are achieved. The loss mechanisms of the ion beam are partly due to elastic scattering and charge exchange, where the ions loose part of their charge. Elastic scattering effects are mitigated by the large velocity difference between the traveling ion and the nearly stationary target gas, that is, the elastic scattering is strongly forward peaked (in scattering angle) due to conservation of momentum. The heavier the ion, especially for large bio-molecules, the more forward peaked the ion scattering becomes, to the point where the collision appears almost not to have occurred. Therefore, even after elastic scattering in the forward direction occurs, the ion can still be focused through the Rotating Field Mass spectrometer and its mass analyzed.

It is also of note that the systems of the invention may operate without any need for magnetic fields.

Forming the mass spectrometer according to the invention enables the device to be smaller, lighter and less costly than other devices of this type. With a Faraday cup electrometer ion detector, sub femtoamp levels of sensitivity may be obtained. Moreover, the device can be made to consume a relatively low level of power. For example a complete device can weigh 1 kg and can consume a mere 10 watts of power.

While the foregoing description of the invention has been presented for the purposes of illustration and description, it is understood that many modifications and variations are possible without departing from the scope or spirit of the present invention. It is intended that the scope of the invention be limited only by the claims appended hereto.

What is claimed is:

1. A rotating field mass spectrometer system, comprising:
    an ionizing structure, comprising a substrate having at least one opening, a first conductive electrode extending on a first surface of the substrate and a second conductive electrode extending on a second surface of the substrate, and a separator insulating element, having a thickness less than 1 micron, separating said first and second conductive electrodes at said at least one opening, said first and second conductive electrodes being separated by a width of said insulator at said opening; and
    a rotating field mass spectrometer part that receives ions from said ionizing structure and which characterizes said ions.

2. A rotating field mass spectrometer system as in claim 1, wherein said first and second conductive electrodes are separated by less than 300 nm at said at least one opening.

3. A rotating field mass spectrometer system as in claim 1, wherein said separator insulating element is a dielectric.

4. A rotating field mass spectrometer system as in claim 3, wherein said separator insulating element is formed of silicon nitride.

5. A rotating field mass spectrometer system as in claim 1, wherein said first and second electrodes are formed of one of gold, chrome or titanium.

6. A rotating field mass spectrometer system as in claim 1, wherein said mass spectrometer system operates at substantially ambient pressure.

7. A rotating field mass spectrometer system as in claim 6, wherein said mass spectrometer system includes a solid-state electrode sensor array that detects ions.

8. A rotating field mass spectrometer system as in claim 1, wherein there are plurality of said thin portions, and said thin portions each formed from first and second conductive electrodes which are separated by said less than 1 micron.

9. A rotating field mass spectrometer system as in claim 1, wherein said first and second conductive electrodes are separated by less than a mean free path of a gas being analyzed.

10. A rotating field mass spectrometer system, comprising:
    an ionizing structure formed of a thick supporting portion with holes formed in the thick supporting portion and having first and second metal electrodes coated on surfaces of the thick supporting portion extending into the holes in the thick supporting portion, where a distance between the first and second metal electrodes within the holes of the thick supporting portion is less than the mean free path of a material being ionized; and
    a rotating field mass spectrometer part, receiving ions formed by said ionizing structure.

11. A method of forming a rotating field mass spectrometer, comprising:
    forming a layer of thin dielectric material on a substrate that has a first specified thickness of a sufficient thickness to maintain structural integrity;

forming a first electrode on the first surface of said thin dielectric material, said first electrode being formed of a metal material;

back etching at least one hole in said substrate;

forming a second electrode on a second surface of the substrate including the at least one back etching holes, such that at least a portion of the second electrode is on a second surface of the thin dielectric material;

forming holes in the second electrode, thin dielectric material and the first electrode, which holes have side surfaces where the first and second electrodes are separated by a width of the thin dielectric material; and forming a rotating field mass spectrometer part to receive ions which have passed through said holes.

12. A method as in claim 11, wherein said thin dielectric material has a thickness which is less than the mean free path of the gas intended to be ionized by the ionizing structure.

13. A method as in claim 11, wherein said forming electrodes comprises depositing gold.

14. A method as in claim 13, wherein said forming a thin dielectric comprises depositing silicon nitride.

15. A method as in claim 11, wherein said thin dielectric has a thickness less than 500 nm.

16. A method as in claim 11, wherein said thin dielectric has a thickness less than 300 nm.

17. A method as in claim 16, further comprising applying a voltage less than 15 volts between said first and second electrodes to form a field between said first and second electrodes in the range of megavolts per meter.

18. A method as in claim 11, wherein said detecting comprises using a pixelated electrometer array to detect said ions.

19. A rotating field mass spectrometer, comprising:

an ionizing structure, having supporting portions, and unsupported parts between said supporting portions, where said unsupported parts include electrodes which are separated by a distance less than the mean free path of a specified sample, and include holes that pass through the ionizing structure; and a rotating field mass spectrometer part, receiving ions from said ionizing structure, and determining characteristics of the ions.

20. A rotating field mass spectrometer system, comprising:

an ionizing structure, comprising a substrate having at least one opening, a first conductive electrode extending on a first surface of the substrate and a second conductive electrode extending on a second surface of the substrate, and a separator insulating element, having a thickness less than 1 micron, separating said first and second conductive electrodes at said at least one opening, said first and second conductive electrodes being separated by a width of said insulator at said opening; and a rotating field mass spectrometer part that receives ions from said ionizing structure and which characterizes said ions;

wherein said separator insulating element is a dielectric having dielectric breakdown of at least $10^7$ volts/meter.

21. A rotating field mass spectrometer system as in claim 20, wherein said separator insulating element has a dielectric breakdown of between $10^8$ and $10^9$ volts/meter.

22. A method of forming a rotating field mass spectrometer, comprising:

depositing a layer of thin dielectric material having a dielectric breakdown of at least $10^7$ volts/meter on a substrate that has a first specified thickness of a sufficient thickness to maintain structural integrity;

forming a first electrode on the first surface of said thin dielectric material, said first electrode being formed of a metal material;

back etching at least one hole in said substrate;

forming a second electrode on a second surface of the substrate including the at least one back etching holes, such that at least a portion of the second electrode is on a second surface of the thin dielectric material;

forming holes in the second electrode, thin dielectric material and the first electrode, which holes have side surfaces where the first and second electrodes are separated by a width of the thin dielectric material; and forming a rotating field mass spectrometer part to receive ions which have passed through said holes.

23. A method of forming a rotating field mass spectrometer, comprising:

depositing a layer of thin dielectric material having a dielectric breakdown of between $10^8$ and $10^9$ volts/meter on a substrate that has a first specified thickness of a sufficient thickness to maintain structural integrity;

forming a first electrode on the first surface of said thin dielectric material, said first electrode being formed of a metal material;

back etching at least one hole in said substrate;

forming a second electrode on a second surface of the substrate including the at least one back etching holes, such that at least a portion of the second electrode is on a second surface of the thin dielectric material;

forming holes in the second electrode, thin dielectric material and the first electrode, which holes have side surfaces where the first and second electrodes are separated by a width of the thin dielectric material; and forming a rotating filed mass spectrometer part to receive ions which have passed through said holes.

* * * * *

UNITED STATES PATENT AND TRADEMARK OFFICE
CERTIFICATE OF CORRECTION

PATENT NO. : 6,921,906 B2  
DATED : July 26, 2005  
INVENTOR(S) : Hartley et al.

It is certified that error appears in the above-identified patent and that said Letters Patent is hereby corrected as shown below:

<u>Column 8,</u>  
Lines 45-46, delete "are plurality of said thing portions, and said thin portions each formed", insert -- are a plurality of said thin portions, and said thin portions are each formed --.

<u>Column 9,</u>  
Line 6, delete "holes", insert -- hole --.

<u>Column 10,</u>  
Line 5, after "having", insert -- a --.  
Lines 20 and 40, delete "holes", insert -- hole --.

Signed and Sealed this

Twenty-eighth Day of March, 2006

JON W. DUDAS  
*Director of the United States Patent and Trademark Office*